(12) United States Patent
Huang

(10) Patent No.: US 7,159,803 B1
(45) Date of Patent: Jan. 9, 2007

(54) METHOD FOR MAKING PARTICULATE COMPOSITIONS AND PRODUCTS THEREOF

(75) Inventor: Yung-Hui Huang, Bel Air, MD (US)

(73) Assignee: J.M. Huber Corporation, Edison, NJ (US)

( * ) Notice: Subject to any disclaimer, the term of this patent is extended or adjusted under 35 U.S.C. 154(b) by 48 days.

(21) Appl. No.: 11/170,344

(22) Filed: Jun. 29, 2005

(51) Int. Cl.
   *B02C 11/08* (2006.01)
(52) U.S. Cl. ......................................... 241/21; 241/24.1
(58) Field of Classification Search .................. 241/21, 241/24.1, 25
   See application file for complete search history.

(56) References Cited

U.S. PATENT DOCUMENTS 5,205,493 A * 4/1993 Adler et al. .................. 241/21

* cited by examiner

*Primary Examiner*—Faye Francis
(74) *Attorney, Agent, or Firm*—William Parks; Carlos Nieves

(57) ABSTRACT

A method of making abrasive compositions, and more particularly, it relates to a method of making precipitated silica abrasive compositions having excellent cleaning performance and lower abrasiveness with post-reactor sizing of the abrasive particles being performed directly via wet comminution and centrifugation, optionally followed by hydraulic chamber press filtering combined with vacuum dewatering and de-agglomeration is provided. By targeting a specific particle size range, it has been determined that higher pellicle film cleaning levels may be achieved without also increasing the dentin abrasion properties of the silica products themselves. As a result, dentifrices including such classified abrasive silica products, exhibiting particularly desirable cleaning benefits, can be provided for improved tooth polishing, whitening, and the like, without deleteriously affecting the hard tooth surfaces. Also encompassed within this invention also are products of this selective process scheme and dentifrices containing such particularly manufactured and classified silica products.

18 Claims, No Drawings

US 7,159,803 B1

METHOD FOR MAKING PARTICULATE COMPOSITIONS AND PRODUCTS THEREOF

FIELD OF THE INVENTION

This invention relates to a method of making abrasive compositions, and more particularly, it relates to a method of making precipitated silica abrasive compositions having excellent cleaning performance and lower abrasiveness with post-reactor sizing of the abrasive particles being performed directly via wet comminution and centrifugation, optionally followed by hydraulic chamber press filtering combined with vacuum dewatering and de-agglomeration. By targeting a specific particle size range, it has been determined that higher pellicle film cleaning levels may be achieved without also increasing the dentin abrasion properties of the silica products themselves. As a result, dentifrices including such classified abrasive silica products, exhibiting particularly desirable cleaning benefits, can be provided for improved tooth polishing, whitening, and the like, without deleteriously affecting the hard tooth surfaces. Also encompassed within this invention also are products of this selective process scheme and dentifrices containing such particularly manufactured and classified silica products.

BACKGROUND OF THE INVENTION

Toothpaste manufacturers strive to produce dentifrices with high cleaning and low abrasivity. Such formulators achieve this goal by incorporating abrasive substances into the toothpaste formulation. An abrasive substance has been included in conventional dentifrice compositions in order to remove various deposits, including pellicle film, from the surface of teeth. Pellicle film is tightly adherent and often contains brown or yellow pigments, which impart an unsightly appearance to the teeth. While cleaning is important, the abrasive should not be so aggressive so as to damage the teeth. Ideally, an effective dentifrice abrasive material maximizes pellicle film removal while causing minimal abrasion and damage to the hard tooth surfaces. Consequently, among other things, the performance of the dentifrice is highly sensitive to the abrasive polishing agent ingredient.

A number of water insoluble, abrasive polishing agents have been used or described for dentifrice compositions. These abrasive polishing agents include natural and synthetic abrasive particulate materials. The generally known synthetic abrasive polishing agents include amorphous precipitated silicas, silica gels, dicalcium phosphate and its dihydrate forms, calcium pyrophosphate and precipitated calcium carbonate (PCC). Other abrasive polishing agents for dentifrices have included chalk, magnesium carbonate, zirconium silicate, potassium metaphosphate, magnesium orthophosphate, tricalcium phosphate, and the like.

Synthetically produced amorphous precipitated silicas, in particular, have been used as abrasive components in dentifrice formulations due to their cleaning ability, relative safety, and compatibility with typical dentifrice ingredients, such as humectants, thickening agents, flavoring agents, anti-caries agents, and so forth. Synthetic precipitated silicas generally are produced by the de-stabilization and precipitation of amorphous silica from soluble alkaline silicate by the addition of a mineral acid and/or acid gases under conditions in which primary particles initially formed tend to associate with each other to form a plurality of aggregates (i.e., discrete clusters of primary particles), but without agglomeration into a three-dimensional gel structure. The resulting precipitate is separated from the aqueous fraction of the reaction mixture by filtering, washing, and drying procedures, and then the dried product is mechanically comminuted in order to provide a suitable particle size.

Such previously produced and utilized precipitated silica abrasives have been produced and provided for dentifrices generally in terms of overall cleaning and abrasive qualities. Although such previous products have accorded excellent benefits in these areas, it has been noted that certain limitations in terms of production costs and waste generation are prevalent as a result. For instance, in order to target specific lower abrasive levels, milled particles include materials that exhibit particle sizes outside the required ranges. Proper filtering and disposal of such undesirable materials are thus needed. The same types of production issues and problems arise when targeting certain lower abrasive levels for particulate materials without sacrificing pellicle film cleaning as well. As it concerns the ability to provide less costly production methods for providing such effective low-abrasion, high pellicle film cleaning materials to users susceptible to unwanted dentin abrasion at the gum line, as well as potential supplemental abrasive/cleaning silica products for more effective polishing and/or tooth whitening applications, the industry has been reliant upon outdated methods of production, separation, and disposal of undesirable particles. As a result, there are areas within the dental silica materials industry in which improvements to such ends are desired.

Given the foregoing, there is a continuing need for a method of producing precipitated silica materials that provide excellent cleaning performance, but with lower abrasivity values, that can be included in a toothpaste composition. To that end, the following invention has proven to accord such coveted results.

BRIEF SUMMARY OF THE INVENTION

It is thus one advantage of this invention to provide an all-inclusive method of manufacturing dental abrasive particles that exhibit proper particle size ranges for effective pellicle film cleaning and moderate dentin abrasion characteristics once manufacturing is completed and said particles are thus collected. Thus, no dry post-reactor comminution or other type of particle modification is necessary to provide the desired particle size ranges for effective high cleaning and moderate dentin abrasion properties exhibited by the produced dental abrasives.

The above and other advantages and benefits are achieved by the present invention directed to a method of making silica compositions with water content reduction and silica particle comminution effected during post-reactor processing under wet conditions.

The basic inventive method entails the production of abrasive compositions, comprised of water-insoluble abrasive polishing agents suspended in an aqueous medium, wherein milling to desired particle size ranges is effectuated via a wet process during actual abrasive product manufacture. Such a method thus avoids the need and associated cost of dry milling the abrasive particle content, and products thereof. It has also been realized that such a wet milling method permits production of appropriately sized abrasive particles and compositions thereof that are rheologically stable, are not prone to settling, and do not exhibit any appreciable level of re-agglomeration, even during and after transport and/or storage before end-use, such as incorporation into dentifrice formulations or other oral cleaning compositions.

Although any known particulate abrasive for dentifrices may be utilized within this invention, particularly preferred are amorphous precipitated silica abrasives. Abrasive compositions including such individual particles should comprise a plurality of silica particles exhibiting a median particle size of about 5 to about 15 microns, preferably from about 6 to about 10, and more preferably from about 7 to about 9, a particle size span of less than or equal to 2, preferably from about 1.25 to about 2.0, and more preferably from about 1.25 to about 1.95.

The invention also includes a dentifrice comprising about 5 wt % to about 35 wt % of the amorphous precipitated silica composition noted above and produced in accordance with such an inventive method, and exhibiting an radioactive dentin abrasion (RDA) level between about 130 and 200 (preferably from about 130 to about 195) and a pellicle film cleaning ratio (PCR) of between about 70 and 140 (preferably from about 80 to about 140).

Basically, it has been realized that the inventive method provides the capability of easily producing low-structure abrasive silica materials within a concentrated range of specific particle sizes permits greater uniformity in performance during tooth cleaning with a dentifrice containing such materials with minimal process steps and thus concomitant lower associated costs. Likewise, providing such materials within the specific range of particle sizes permits targeting particular areas of tooth surfaces for proper cleaning without simultaneously exhibiting excessive abrasive levels.

DETAILED DESCRIPTION OF THE INVENTION

All parts, percentages and ratios used herein are expressed by weight unless otherwise specified. All documents cited herein are incorporated by reference. The following describes preferred embodiments of the present invention, which provides silica for use in dentifrices, such as toothpastes. While the optimal use for this silica is in dentifrices, this silica may also be used in a variety of other consumer and industrial products, such as cosmetics and coatings. In these other products, the same process is used, however a different particle size fraction of particles is isolated, such as smaller particles, depending on the final use requirements.

By "mixture" it is meant any combination of two or more substances, in the form of, for example without intending to be limiting, a heterogeneous mixture, a suspension, a solution, a sol, a gel, a dispersion, or an emulsion.

By "dentifrices" it is meant oral care products such as, without intending to be limiting, toothpastes, tooth powders and denture creams.

For the purposes of defining this invention, the term "particle size span" is intended to mean the cumulative diameter of the particles in the tenth volume percentile (D10) minus the cumulative volume at the ninetieth percentile (D90) divided by the diameter of the particles in the fiftieth volume percentile (D50), i.e. (D10–D90)/D50. A lower span value indicates a narrower particle size distribution.

The present invention relates, particularly, to amorphous, precipitated silica compositions, also known as silicon dioxide, or $SiO_2$, which impart improved cleaning and abrasive characteristics when included within a toothpaste or dentifrice. These abrasive silicas not only clean teeth by removing debris and residual stains, but also function to polish tooth surfaces. Because the silicas of the present invention have been classified to remove fine particles which are believed to have less cleaning benefit and large particles which are believed to contribute to increased abrasion, they have a narrower particle size distribution and are particularly useful for formulating a dentifrice that has excellent cleaning with lower abrasivity. Other possible abrasive products that may be produced through the inventive process include, without limitation, precipitated calcium carbonate (PCC), silica gels, dicalcium phosphate and its dihydrate forms, and calcium pyrophosphate. Such particles are engineered to provide excellent cleaning benefits for dental applications. Such cleaning characteristics are generally measured as pellicle film cleaning ratios (PCR), and are discussed in greater detail below, particularly in conjunction with other abrasive measurements.

A sufficient amount of abrasive silica should be added to a toothpaste composition so that the radioactive dentin abrasion ("RDA") value of the toothpaste is between about 50 and about 250. At a RDA of less than 50, the cleaning benefits of the toothpaste will be minimal, while at a RDA of greater than 250, there is risk that the toothpaste will be so abrasive that it may damage the tooth dentin along the gum line. Preferably, the dentifrice should have a RDA value of at least about 50, such as between about 70 and 200.

The RDA of a toothpaste is dependent on the hardness of the abrasive, the abrasive particle size and the concentration of the abrasive in the toothpaste. The RDA is measured by the method described in the article "A Laboratory Method for Assessment of Dentifrice Abrasivity", John J. Hefferren, in *Journal of Dental Research*, Vol. 55, no. 4 (1976), pp. 563–573. Silica abrasivity or hardness can also be measured by an Einlehner method, which is described in greater detail below.

By the present invention, abrasive amorphous silicas have been developed that not only have excellent cleaning performance (in terms of PCR measurements) but are also less abrasive than typically produced products. By using the inventive wet milling, all-inclusive abrasive particle composition production method, an abrasive material (such as, preferably, though not necessarily an amorphous precipitated silica product) may be produced that has relatively low RDA and Einlehner abrasion values over a given PCR range.

Accordingly, the particulate compositions (and the preferred abrasive particles, and more preferred abrasive amorphous precipitated silica compositions) of the present invention are prepared according to the following first process comprising the sequential steps of:

a) providing a plurality of particles selected from the group consisting of precipitated silica particles, silica gel particles, precipitated calcium carbonate particles, calcium pyrophosphate particles, dicalcium phosphate, and any mixtures thereof;

b) subjecting said plurality of particles to a comminuting step in a wet environment;

c) subjecting said wet-comminuted particles to a particle size classification step wherein particles exhibiting a median particle size range of from about 5 to about 30 microns are collected;

d) subjecting said collected particles from step "c" to a subsequent particle size classification step wherein particles exhibiting a median particle size range of from about 5 to about 15 microns are collected; optionally e) subjecting said collected classified particles from step "d" to a dewatering step wherein said dewatered particles exhibit a moisture content of at most 60 wt %; and, optionally f) subjecting said dewatered abrasive particles to a deagglomeration step.

Such process steps are discussed in greater detail below.

Alternatively, a second inventive method may encompass the sequential steps of:

a) providing a plurality of precipitated silica particles that have not previously been dried prior to commencement of step "b";

b) subjecting said plurality of particles to a comminuting step in a wet environment;

c) subjecting said wet-comminuted particles to a particle size classification step wherein particles exhibiting a median particle size range of from about 0.1 to about 15 microns are collected;

d) subjecting said collected classified particles from step "c" to a dewatering step wherein said dewatered particles exhibit a moisture content of at most 60 wt %; and, optionally e) subjecting said dewatered abrasive particles to a deagglomeration step.

Such process steps are also discussed in greater detail below.

In the first step of the first method outlined above (and as can be followed for the second method), at least for the production of precipitated silica abrasives, an acidulation reaction is performed to precipitate silica. The initial acidulation reaction is performed in a reaction system equipped with suitable heating equipment. In general, the precipitated silicas made in step "a" may be prepared by a fresh water, or electrolyte solution, acidulation process wherein silica is precipitated by reaction of an alkali metal silicate and a mineral acid in aqueous solution. In the fresh water process, no electrolyte such as alum, $Na_2SO_4$, or NaCl, is present during the acidulation reaction.

A portion of the sodium silicate solution is charged to a reactor container or chamber including agitator means to provide agitation to the container contents. Preferably, about 0% to 30% of the total stoichiometric amount of sodium silicate solution is placed in the reactor container to serve as initiating nuclei for the silica. The aqueous solution of sodium silicate in the container is then preheated to a temperature in the range of about 60 to 100° C., more preferably about 80 to 95° C. Prior to introduction into the reactor container, the remaining sodium silicate is preferably preheated to about 70 to 95° C. The acid solution temperature is preferably ambient.

Although sodium silicate is illustrated, it will be understood that any suitable alkali metal silicate could be used. The term "alkali metal silicate" includes all the conventional forms of alkali silicates, as for example, metal silicates, disilicates and the like. Water soluble potassium silicates and sodium silicates are particularly advantageous with the latter being preferred. It should be taken into consideration that the mole ratio of the alkali silicate, i.e., the ratio of silica to alkali metal oxide, contributes, depending on other reaction parameters, to the average pore size of the silica products. In general, acceptable silica products of this invention can be made with silicate molar ratios ($SiO_2:Na_2O$) ranging from about 1.0 to 3.5 and preferably from about 2.4 to about 3.4. The alkali silicate solution supplied to the reactor vessel during various processing steps in the inventive method, as described elsewhere herein, generally can contain between about 8 to 35%, and more preferably between about 8.0% and 25.0%, by weight alkali metal silicate based on the total weight of the alkali metal silicate solution. In order to reduce the alkali silicate concentration of a source solution of alkali silicate to the above-indicated desired range, dilution water can be added to a source solution of alkali silicate before the silicate solution is fed into the reactor, or, alternatively, the dilution water can be combined in situ with the source solution of alkali silicate in the reactor used in the acidulation reaction step "a" with agitation-mixing to formulate the desired concentration of silicate in the alkali metal silicate solution.

The acid, or acidulating agent, can be a Lewis acid or Brönsted acid, and preferably is a strong mineral acid such as sulfuric acid, hydrochloric acid, nitric acid, phosphoric acid, and so forth, and more preferably sulfuric acid, added as a dilute solution thereof (e.g., at a concentration of between about 6 to 35 wt %, more typically about 9.0 to 20.0 wt %).

Once the reactor solution and remaining reactants have reached the desired temperatures, simultaneous addition of the remaining sodium silicate solution and acid into the reactor is commenced. The sodium silicate solution and acid are metered into the reactor over an addition time of about 30 to 90 minutes. Rates of addition of the reactants depend upon the mole ratio, addition time and concentration of the silicate and the concentration of the acid.

At the end of this co-addition period, most of the silica has precipitated and the sodium silicate addition is stopped. Addition of the acid is continued until the reactor slurry reaches the desired pH. Once the slurry pH reaches about 7.0, it is preferable to reduce the acid flow rate until the slurry pH approaches the target pH, at which point the acid flow can be stopped and manual adjustment used to reach the target slurry pH. The preferred slurry pH is approximately 4.0 to 7.0, and more preferably between 5.0 to 6.0. At this juncture, the silica has precipitated to provide a mixture of the precipitated silica and the reaction liquor. Once the desired slurry pH is reached, digestion begins and the reaction temperature is raised to approximately 85–99° C., and preferably 91 to 97° C., and digestion is continued at the elevated temperature for approximately 5 to 60 minutes, and preferably for approximately 10 to 20 minutes. Acid is added during the digestion step to the extent necessary to maintain a constant pH.

After the digestion step is completed in the reactor, and any subsequent pH adjustment conducted, the reaction batch is discharged from the reactor. Although the above-described general protocol are preferred for synthesizing the precipitated silica to be conditioned according to this invention, it will be appreciated that other grades of precipitated silicas, such as very low to high structure synthetic silicas in accordance with the definitions set forth in J. Soc. Cosmet. Chem., 29, 497–521 (August 1978), and Pigment Handbook: Volume 1, Properties and Economics, 2nd ed., John Wiley & Sons, 1988, p. 139–159, generally can be used in the practice of this invention.

In the second method, at least, it is imperative that the subject silica particles not be subjected to any drying prior to step "b" commencing. Basically, if the particles have been dried previously, the structure prior to comminution (wet or otherwise) would be significantly different from that needed for the inventive method to ultimately provide suitable precipitated silica particles for the noted end uses. Such a limitation, though not necessary within the first method discussed, is nonetheless a potentially preferred requirement therein as well.

In step "b" of either the first or second method, wet comminuting of the reaction mass is performed. Comminution is needed because the silica particles suspension drawn from the reactor of step "a" generally have a median particle size (MPS) of greater than about 50 μm to about 100 μm, and more typically about 65 μm to about 85 μm. These particles sizes are unacceptable for applications such as cosmetics, coatings and oral cleaning compositions. Namely, smaller silica particles are needed so that the particles are not gritty in texture to a user, yet for oral care use the particles must be large enough to provide the requisite polishing action on teeth. For oral cleaning compositions, silica particle sizes between about 1 and about 30 μm are generally required, and a median particle size of between about 3 to 15 μm is preferred in this invention. For cosmetic and coating uses, the median particle size range would be smaller, such as from 0.1 to about 3 microns. Thus, a range of from 0.1 to 15 is suitable for the products of this invention (more particularly between 0.3 and 10; for preferred oral care end-uses, the range is preferably from 7 to 9 microns).

Prior to the wet comminution (i.e., wet milling) step of either first or second method, it is important that the silica particles not be subjected to any prior controlled milling procedures (such controlled milling would not include shearing during particle production within a reactor). The controlled comminution of the silica particle in a wet environment permits greater reliability in producing the desired particle size ranges as well as reliability in terms of modifying each particle in the same manner and under the same conditions.

Such comminution is performed, as noted above, through a wet grinding step in a separate station from particle production, or, as an alternative, via high shear reactor mixing during and/or after silica particle production. Preferably, in order to comminute the abrasive particles (typically agglomerates) in step "b", the particles (preferably, though not necessarily, precipitated silica particles) of step "a" are fed to a wet media grinding station. Either a single stage wet media mill or a multi-stage wet milling operation in step "b" can be used. For example, the multi-stage wet media grinding station, in one embodiment, can be comprised of two or more separate mills through which the slurry is successively progressed. Alternatively, the multi-stage wet media grinding station can be comprised of a single mill in which the slurry is fed through the single mill in multiple passes using recirculation. The amount of energy dissipated into the feed slurry at each mill stage, or in each pass through a single mill in a multi-pass form of multi-stage milling, generally is kept approximately the same, although this is not necessarily required. Multi-stage wet media milling permits longer residence times to be applied.

The wet media mill types used as the mill or mills described above in the multi-stage grinding station independently can be ball mills, wet vertical media mills, wet horizontal media mills and the like. One preferred type of wet grinding mill used in the practice of this invention is a Model HML 1.5 Premiere Mill manufactured by Lightnin, Inc., Reading, Pa. The Premier mill is a horizontal style media mill. The milling media used preferably are ceramic beads, e.g., zirconium oxide beads, of about 1 to 3 mm in size, which are loaded in the mills at about 20 to 80 vol %.

In one preferred non-limiting illustration, the wet bead mill used to conduct step "b" generally is operated under the following conditions:

Bead loading: 20–60%; and
Bead mill rotor speed: 500–3500 FPM (feet per minute) (152–1067 m/minute).

In keeping with an objective of this invention of reducing silica particles without the need for drying and dry milling procedures, the total amount of shearing forces applied to the slurry or fluidized press cake during wet grinding should be sufficient to reduce the median particle size (MPS) to between about 0.1 to about 30 microns (μm), preferably between about 1 and about 25 microns, and more preferably between about 3 and about 15 microns. The abrasive particles in the wet milled abrasive composition have less than 1.5 wt % fraction of particles greater than 45 μm (+325 mesh). Of course, the milling conditions can be adjusted to achieve the particle size desired for a particular application.

Alternately, the silica particles of step "a" are first filtered and washed before being fed to the grinding station of step "b" (if such a grinding station is used). The silica reaction slurry produced in step "a" typically contains about 6 to 12 wt. % silica particles, which may be increased to about 12 to 50 wt. % silica particles by filtration. The particles may be collected and washed to remove reaction by-products (e.g. sodium sulfate) on any batch or continuous filtration device known to one skilled in the art, such as vacuum and pressure filters, e.g. rotary filter, belt filter, Larox filter, plate and frame filter, or filter press.

In step "c" or either of the first or second methods outlined above, the comminuted particles (preferably, milled precipitated silica particles) of step "b" were thereafter fed at a rate of about 0.5–10 LPM into a decanter centrifuge, such as a 6-inch solid bowl continuous flow Bird decanter/centrifuge available from Bird Machine Company, Inc., South Walpole, Mass., to isolate particle fractions of desired size. The decanter centrifuge, operated at 20–70 HZ, can be configured with both of the underflow (larger particles) and overflow (smaller particles) streams recirculated or only one flow recirculated to the centrifuge/decanter or to the mill. The milling-centrifuge/decanter combination may be either a single stage combination or a multi-stage combination. The inventive process contemplates isolating smaller particle fractions, larger particle size fractions and isolating particles that have been "double cut", that is, where particles above a desired particle size range are removed and particles below a desired particle size range are removed leaving only particles of a narrow desired particle size range.

In one embodiment, the larger particles from the centrifuge/decanter underflow stream is fed into a mill for further particle size reduction and thereafter fed back into a centrifuge decanter. This "closed loop" system has the effect of continuously reducing the particle size of the larger undesirable particles and the recycling continues until desired particle size ranges are obtained. The time necessary to achieve desired particle size ranges depends upon many factors, such as feed rate, mill energy, bead loading, silica particle structure, and the like. In this embodiment, underflow stream (coarse) is recycled back to the mill while the overflow (fines) is collected for use or further processing.

In another embodiment, the silica particles are "double cut", that is the undesirable fraction of larger (coarse) particles as well as the fraction of undesirable smaller (fines) particles are removed or "cut" from the desirable sized particles. In this case, the underflow (coarse) particles are fed back into the bead mill for further particle size reduction and the overflow (fines) particles are collected for further classifying. Recycling of the underflow stream from the centrifuge/decanter to the mill continues until the desired particle sized materials is obtained. Finally, when the particle distribution reaches the desired particle size, the overflow (fines) stream is discarded and the underflow (coarse) particles are collected. The centrifuge/decanter conditions such as feed rate, concentration, and centrifuge speed can be adjusted to obtain the desired sized particles in the minimum amount of time. Feed rate is generally about 0.5 LPM to about 10 LPM. Concentration of the feed is generally about 6 wt. % to about 50 wt. %, preferably about 10 wt. % to about 40 wt. %. Centrifuge speed is set dependent on the type of equipment used, the desired particle size, particle size distribution and particle size range.

The stream from either the underflow or the overflow can be collected for use as such or used as a feed for further optional processing. The resultant slurry was about 6 wt % to about 50 wt % solids, preferably about 30 wt. % to about 50 wt. % solids.

The classifier may be configured for any range of particle sizes. Preferably, for particles to be utilized as dental abrasives, this configuration permits collection of particles exhibits ranges in particle size from 5 to 15 microns, preferably from 6 to 10, and most preferably from 7 to 9. For cosmetic, and other types of end-uses wherein the particle sizes should be much smaller, the classifier should be configured for collection of particles exhibits particle size ranges from 0.1 to 10 microns, preferably from 0.3 to 5, and most preferably from 0.5 to 2.5.

Additionally, the classified silica slurry of step "c" (in either the first or second method outlined above) can be used as such, mixed with other ingredients such as a humectant, (e.g. glycerin or sorbitol), preservative, fluoride source or the like for use in a dentifrice or dewatered and washed.

In step "d" of the inventive process (optional in the first outlined method, required in the second, as noted above), the classified silica slurry of step "c" is next dewatered. In one preferred aspect, so-called "J-Vap" processing, or similar chamber filter press processing, is preferred in the implementation of step "d" of the preferred embodiment of the invention.

Non-limiting illustrations of methods and equipment arrangements for conducting such J-Vap processing that can be adapted for use in the practice of the filtering/dewatering step of the present invention can be found, for example, in U.S. Pat. No. 5,558,773 and EP 0 978 304 A2, which descriptions are incorporated herein by reference. Other examples of J-Vap processing equipment include commercially available equipment for this purpose, such as that illustrated in the working examples below. The J-Vap processing equipment employed must permit reliable and accurate control over the level of water removal to meet the criterion set forth herein for that parameter.

The J-Vap processing arrangement generally includes a series of reduction chambers in which the washing and dewatering of the silica slurry is conducted. The reduction chambers are tightly clamped together in the filter press module. An energy conversion module also is included that supplies heated water for the pressurization of the reduction chambers and also includes a vacuum system used during dewatering performed after an initial pressure filtering stage.

In one exemplary suitable arrangement, the chamber filter press of the J-Vap processing system is selected as including a plurality of alternating diaphragm squeeze plates and filter plates covered by respective liquid-permeable filter membranes, in which the squeeze plates and filter plates define abrasive suspension introduction and flow passages therebetween, wherein the squeeze plates include a diaphragm that is expandable toward an adjoining filter plate effective to increase solid/liquid separation in the abrasive suspension in which liquid is transmitted through the adjoining liquid-permeable membrane, and the filter plates including respective interior filtrate drainage chambers for drainage of liquid filtered from the abrasive suspension.

During an initial filtering stage performed on abrasive slurry supplied from the classifier, the slurry wet cake is washed with water, then air blow down commences to remove surface water from the cake. The initial or "core" blow down may be performed in a single step or in a pulsed manner, wherein air is blown for a set time, stopped and repeated for a set number of times. Thereafter, the diaphragm is expanded by introduction of heated fluid effective to expand the diaphragm and heat the abrasive suspension effective to promote water removal from the filter material. That is, slurry from the classifier is pumped into the reduction chambers where initial filtration occurs and the free liquid is drained away. After the initial filtration stage, vacuum-promoted dewatering is performed. For example, the reduction chambers are pressurized with heated water, and a vacuum is introduced. For example, in a second stage of the dewatering process as performed in the J-Vap processing system, the drainage chambers are connected to a vacuum source effective to remove vaporized portions of the abrasive suspension.

The dewatering time is set to achieve the desired water reduction. After the dewatering stages are completed, the reduction chambers are separated from one another and the dewatered filter cake material is discharged and proceeds to the de-agglomeration step.

Illustrative, non-limiting conditions for conducting such J-Vap dewatering, when used to perform the dewatering step "d" according to the preferred embodiment of the invention, include the following general conditions:

De-water time: 0 to 6 hours;
Feed Pressure: 20–80 psi (138–552 kPa);
Feed temp: 21–85° C.;
Hot water temp: 49–85° C. (120–185° F.);
Blow down air pressure: 20–80 psi (138–552 kPa);
System Vacuum: 20–29 in. Hg (68–98 kPa);
Squeeze air pressure: 20–100 psi (138–552 kPa); and
Solids content out of J-Vap: 40–95%.

The reaction mass is filtered and washed with water to reduce the $Na_2SO_4$ level to less than 5%, and preferably less than 2%, by weight (e.g., 0.5 to 1.5%). The resulting dewatered mass generally comprises about 70 to about 95 weight percent of silica particles, and from about 5 to about 30 weight percent water (preferably 5 to 10 wt. % water). The pH of the washed filter cake can be adjusted, if necessary.

Alternately, the classified silica of step "c" can be washed and dewatered utilizing a vacuum or pressure filter.

The dewatered silica particles resulting from step "d" generally have agglomerated due to the pressure applied during the dewatering process. This is typically a weak particle agglomeration such that the particles may be separated when incorporated into a formulation, such as a dentifrice or cosmetic formulation. De-agglomeration may be achieved in optional step "e" by exposing the particles to gentle dry mixing such as airveying the particles, feeding the particles into a mill configured with no hammers or whizzards, high shear mixing, or the like.

The finished abrasive at step "e" (in either first or second method), having water content reduced to about less than 10% can be stored until needed for later usage, such in the preparation of dentifrices or other cosmetic, personal care or coating compositions.

An important aspect of this invention is that the milled, classified particles (preferably abrasive silica particles) provided at step "e" can be continuously maintained at a total liquid content of at least 5 wt %, up until an additional step of incorporating said abrasive particles into a dentifrice composition or other cosmetic, personal care or coating composition without the need to dry the silica or perform dry milling. No drying or dry milling of the precipitated silica need occur from the time the silica is synthesized up until its incorporation into an oral cleaning composition. While not desiring to be bound to any particular theory at this time, it is postulated that drying and dry milling processes impact the surface and chemical properties of the silica particles in unpredictable or even adverse manners, e.g. discoloration from dry milling. The present invention avoids these impacts of drying and dry milling.

The preferred silica particles provided in the above-illustrated abrasive compositions are preferably characterized as synthetic hydrated amorphous silicas, known as silicon dioxides or $SiO_2$. These precipitated silicas can be characterized as very low to high structure synthetic silicas.

In addition to the above-described step "a" methodology of precipitating the raw synthetic amorphous silicas in the reactor, the preparation of the raw silica is not necessarily limited thereto and it also can be generally accomplished in accordance with the methodologies described, for example, in prior U.S. Pat. Nos. 3,893,840, 3,988,162, 4,067,746, 4,340,583, 5,225,177, 5,891,421, and 6,419,174 all of which are incorporated herein by reference, as long as such methods are appropriately modified to append the post-processing treatment(s) used in at least steps "b" and "c" of the preferred inventive method, as discussed above. As will be appreciated by one skilled in the art, reaction parameters which affect the characteristics of the resultant precipitated silica include: the rate and timing at which the various reactants are added; the levels of concentration of the various reactants; the reaction pH; the reaction temperature; and/or the rate at which any electrolytes are added.

Although silicas have been illustrated herein as the abrasive polishing agent component provided in the abrasive compositions being produced by this invention, it will be understood that the principles of the present invention are also considered applicable to suspensions or slurries of other water-insoluble abrasive particles that can be synthesized in a reactor without the need for any intervening drying or dry milling steps. Other such water-insoluble particles include, for example, silica gels, dicalcium phosphate or its dihydrate forms, calcium pyrophosphate and precipitated calcium carbonate (PCC).

Examples of use of these optional dentifrice ingredients are described herein and/or, for example, in Reissue 29,634, and U.S. Pat. Nos. 5,676,932, 6,074,629, and 5,658,553, and the patents cited therein, all being incorporated herein by reference. These optional ingredients, if used, can be used at levels that are customarily seen in dentifrice formulations.

As noted above, the abrasive particles produced by this inventive method (in particular, though not required, said amorphous precipitated silica abrasives) may then be incorporated into a dentifrice composition, e.g., toothpaste.

In addition to the abrasive component, such a dentifrice may also contain several other ingredients commonly used in dentifrice making such as humectants, thickening agents, (also sometimes known as binders, gums, or stabilizing agents), antibacterial agents, fluorides, sweeteners, and co-surfactants.

Humectants serve to add body or "mouth texture" to a dentifrice as well as preventing the dentifrice from drying out. Suitable humectants include polyethylene glycol (at a variety of different molecular weights), propylene glycol, glycerin (glycerol), erythritol, xylitol, sorbitol, mannitol, lactitol, and hydrogenated starch hydrolyzates, as well as mixtures of these compounds.

Thickening agents are useful in the dentifrice compositions of the present invention to provide a gelatinous structure that stabilizes the toothpaste against phase separation. Suitable thickening agents include silica thickener, starch, glycerite of starch, gum karaya (sterculia gum), gum tragacanth, gum arabic, gum ghatti, gum acacia, xanthan gum, guar gum, veegum, carrageenan, sodium alginate, agar—agar, pectin, gelatin, cellulose, cellulose gum, carboxymethyl cellulose, hydroxyethyl cellulose, hydroxypropyl cellulose, hydroxymethyl, hydroxymethyl carboxypropyl cellulose, methyl cellulose, ethyl cellulose, sulfated cellulose, as well as mixtures of these compounds. Typical levels of binders are from about 0 wt % to about 15 wt % of a toothpaste composition.

Antibacterial agents may be included to reduce the presence of microorganisms to below known harmful levels. Suitable antibacterial agents include tetrasodium pyrophosphate, benzoic acid, sodium benzoate, potassium benzoate boric acid phenolic compounds such as betanapthol, chlorothymol, thymol, anethole, eucalyptol, carvacrol, menthol, phenol, amylphenol, hexylphenol, heptylphenol, octylphenol, hexylresorcinol, laurylpyridinium chloride, myristylpyridinium chloride, cetylpyridinium fluoride, cetylpyridinium chloride, cetylpyridinium bromide. If present, the level of antibacterial agent is preferably from about 0.1 wt % to about 5 wt % of the toothpaste composition.

Sweeteners may be added to the toothpaste composition to impart a pleasing taste to the product. Suitable sweeteners include saccharin (as sodium, potassium or calcium saccharin), cyclamate (as a sodium, potassium or calcium salt), acesulfame-K, thaumatin, neohisperidin dihydrochalcone, ammoniated glycyrrhizin, dextrose, levulose, sucrose, mannose, and glucose.

The toothpaste will also preferably contain fluoride salts to prevent the development and progression of dental caries. Suitable fluoride salts include sodium fluoride, potassium fluoride, zinc fluoride, stannous fluoride, zinc ammonium fluoride, sodium monofluorophosphate, potassium monofluorophosphate, laurylamine hydrofluoride, diethylaminoethyloctoylamide hydrofluoride, didecyldimethylammonium fluoride, cetylpyridinium fluoride, dilaurylmorpholinium fluoride, sarcosine stannous fluoride, glycine potassium fluoride, glycine hydrofluoride, and sodium monofluorophosphate. Typical levels of fluoride salts are from about 0.1 wt % to about 5 wt %.

Surfactants may also be included as additional cleansing and foaming agents, and may be selected from anionic surfactants, zwitterionic surfactants, nonionic surfactants, amphoteric surfactants, and cationic surfactants. Anionic surfactants are preferred, such as metal sulfate salts, such as sodium lauryl sulfate.

The dentifrices disclosed herein may also contain a variety of additional ingredients such as desensitizing agents, healing agents, other caries preventative agents, chelating/sequestering agents, vitamins, amino acids, proteins, other anti-plaque/anti-calculus agents, opacifiers, antibiotics, anti-enzymes, enzymes, pH control agents, oxidizing agents, antioxidants, whitening agents, colorants, flavorants, and preservatives.

Finally, water provides the balance of the composition in addition to the additives mentioned. The water is preferably deionized and free of impurities. The dentifrice will comprise from about 10 wt % to about 40 wt % of water, preferably from 20 to 35 wt %.

Furthermore, smaller particle size particles may either be produced via the second outlined method or as byproducts of the first outlined method. Such smaller particles, preferably, again, silica particles, may be incorporated within a variety of compositions and formulations, such as within cosmetics and like end-uses, wherein such small particles may be present as pigments, detackifiers, carriers, and the like.

DETAILED DESCRIPTION OF THE PREFERRED EMBODIMENTS

The abrasive compositions made by the method of the present invention are storable, ready-to-use abrasive particles and slurries that can be readily formulated on demand with other ingredients to prepare oral cleaning compositions having a high cleaning efficacy without causing undue abrasion on tooth tissues. The essential as well as optional steps of the inventive method are described in more detail below.

Particulate Composition Production

The following examples are presented to illustrate the invention, but the invention is not to be considered as limited thereto. In the following examples, parts are by weight unless indicated otherwise.

The silica properties described herein were measured as follows. Median particle size was determined using a Model LA-910 laser light scattering instrument available from Horiba Instruments, Boothwyn, Pa. A laser beam is projected through a transparent cell which contains a stream of moving particles suspended in a liquid. Light rays which strike the particles are scattered through angles which are inversely proportional to their sizes. The photodetector array measures the quantity of light at several predetermined angles. Electrical signals proportional to the measured light flux values are then processed by a microcomputer system to form a multi-channel histogram of the particle size distribution. Samples are subjected to 2 minutes ultrasonics on the Horiba instrument prior to analysis.

The size distribution of silica particles in a given composition is plotted as cumulative volume percent as a function of particle size. Cumulative volume percent is the percent, by volume, of a distribution having a particle size of less than or equal to a given value and where particle size is the diameter of an equivalent spherical particle. The mean particle size in a distribution is the size in microns of the silica particles at the 50% point for that distribution. The width of the particle size distribution of a given composition can be characterized using a span ratio. As used herein, the span ratio is defined as the cumulative diameter of the particles in the tenth volume percentile minus the cumulative volume at the ninetieth percentile divided by the diameter of the particles in the fiftieth volume percentile, i.e. (D10−D90)/D50.

Oil absorption, using linseed oil, was determined by the rubout method. This method is based on a principle of mixing oil with silica by rubbing with a spatula on a smooth surface until a stiff putty-like paste is formed. By measuring the quantity of oil required to have a paste mixture which will curl when spread out, one can calculate the oil absorption value of the silica, which is the value which represents the volume of oil required per unit weight of silica to saturate the silica sorptive capacity. For purposes of the oil absorption measurement, the silica sample tested was obtained directly from the silica product of the J-Vap procedure and dried at 105° C. for about 12 hours before testing. Calculation of the oil absorption value was done as follows:

$$\text{Oil absorption} = \frac{\text{ml oil absorbed}}{\text{weight of silica, in grams}} \times 100$$

$$= \text{ml oil}/100 \text{ gram silica}$$

A 5% pH was determined by weighing 5.0 grams silica into a 250-mL beaker, adding 95 ml of deionized or distilled water, mixing for 7 minutes on a magnetic stir plate, and measuring the pH with a pH meter which has been standardized with two buffer solutions bracketing the expected pH range.

Sodium sulfate content was determined by comparison of the sample conductivity with a standard curve generated from known sodium sulfate/silica composition slurries. Into a one-quart mixer cup of a Hamilton Beach Mixer, Model Number 30, 38 g of silica wet cake sample was weighed, 140 ml of deionized water was added and the slurry was mixed for 5 to 7 minutes. The slurry was transferred to a 250-ml graduated cylinder and made up to volume to 250 ml with deionized water, using the water to rinse out the mixer cup. The sample was mixed by inverting the graduated cylinder several times. Conductivity of the slurry was determined using a conductivity meter, such as a Cole Palmer CON 500 Model #19950-00.

To measure the % 325 sieve residue, 50 g silica was weighed into a 1-liter beaker containing 500–600 ml water. The silica was allowed to settle into the water, then mixed well until all the material was dispersed. The water pressure through the spray nozzle (Fulljet 9.5, ⅜ G, 316 stainless steel, Spraying Systems Co.) was adjusted to 20–25 psi. The sieve screen cloth (325 mesh screen, 8" diameter) was held 4–6 inches below the nozzle and, while spraying, the beaker contents was gradually poured onto the 325 mesh screen. The remaining material was rinsed from the walls of the beaker and poured onto the screen. The screen was washed for 2 minutes, moving the spray from side to side in the screen using a sweeping motion. After spraying for 2 minutes (all particles smaller than the screen opening should have passed through the screen), the residue retained on the screen was washed to one side, and then transfer into a pre-weighed aluminum weighing dish by washing with water from a squirt bottle. A minimum amount of water needed to be sure all the residue was transferred into the weighing dish was used. The dish was allowed to stand 2–3 minutes (residue settles), then the clear water was decanted off the top. The dish was placed in an oven ("Easy-Bake" infrared oven or 105° C. oven) and dried until the residue sample was dried to a constant weight.

$$\% \text{ 325 residue} = \frac{\text{weight of residue, g}}{\text{sample weight, g}} \times 100 = \% \text{ particles} > 45 \ \mu m$$

To determine loose bulk density, 100 g of silica was gently poured into a 100-mm polypropylene powder funnel clamped with the aperture 1.5 inches above the top of a 250-ml polymethylpentene graduated cylinder, which had been cut off at the 100-ml marking and pre-weighed. The flow of silica is stopped when the cylinder was overflowing. The powder in the graduated cylinder was immediately leveled by scraping across the top of the cylinder with a spatula. This step should be done as quickly as possible to prevent settling of the powder bed which would give artificially high values. Excess powder was brushed from the base of the graduated cylinder and the filled cylinder was weighed to 0.01 g accuracy. Volume change in the cylinder due to handling is ignored.

Loose Bulk Density (g/ml)=(total wt.−initial wt.)/100

Pack or tapped density was determined by weighing 20.0 grams of product into a 250-mL plastic graduated cylinder with a flat bottom. The cylinder was closed with a rubber stopper and placed on a tap density machine and run for 15 minutes. The tap density machine is a conventional motor-gear reducer drive operating a cam at 60 rpm. The cam is cut or designed to raise and drop the cylinder a distance of 2.25 inch (5.715 cm) every second. The tapped density was calculated as the volume occupied by a known weight of product and expressed in g/ml.

Mercury pore volume was determined using an Autopore II 9220 Porosimeter (Micromeritics Corporation). This instrument measures the void volume and pore size distribution of various materials. Mercury is forced into the voids as a function of pressure and the volume of mercury intruded per gram of sample is calculated at each pressure setting. Total pore volume expressed herein represents the cumulative volume of mercury intruded at pressures from vacuum to 60,000 psi.

To measure brightness, fine powder materials pressed into a smooth surfaced pellets were evaluated using a Technidyne Brightmeter S-5/BC available from Technidyne Corporation, New Albany, Ind. This instrument has a dual beam optical system where the sample is illuminated at an angle of 45°, and the reflected light viewed at 0°. It conforms to TAPPI test methods T452 and T646, and ASTM Standard D985. Powdered materials are pressed to about a 1 cm thick pellet with enough pressure to give a pellet surface that is smooth and flat and without loose particles or gloss.

The Brass Einlehner (BE) Abrasion value was measured through the use of an Einlehner AT-1000 Abrader. In this test, a Fourdrinier brass wire screen is weighed and exposed to the action of a 10% aqueous silica suspension for a fixed number of revolutions, and the amount of abrasion was then determined as milligrams brass lost from the Fourdrinier wire screen per 100,000 revolutions. Disposable supplies required for this test (brass screens, wear plates and PVC tubing) are available from Duncan Associates, Rutland, Vt. and sold as an "Einlehner Test Kit". Specifically, brass screens (Phosphos Bronze P.M.) were prepared by washing in hot, soapy water (0.5% Alconox) in an ultrasonic bath for 5 minutes, then rinsing in tap water and rinsing again in a beaker containing 150 ml water set in an ultrasonic bath. The screen was rinsed again in tap water, dried for 20 minutes in an oven set at 105° C., cooled in a desiccator and weighed. Screens are handled with tweezers to prevent skin oils from contaminating the screens. The Einlehner test cylinder was assembled with a wear plate and weighed screen (red line side down—not abraded side.) and clamped in place. The wear plate was used for about 25 tests or until worn badly; the weighed screen was used only once.

A 10% silica slurry, prepared by mixing 100 g silica with 900 g deionized water, (or in the case of silica slurry, 227 g of silica slurry at 45% solids was mixed with 773 g water) was poured into the Einlehner test cylinder. Einlehner PVC tubing was placed onto the agitating shaft. The PVC tubing has 5 numbered positions. For each test, the position of the PVC tubing was incremented until it has been used five times, then discarded. The Einlehner abrasion instrument was re-assembled and the instrument set to run for 87,000 revolutions. Each test takes about 49 minutes. After the cycle was completed, the screen was removed, rinsed in tap water, placed in a beaker containing water and set in an ultrasonic bath for 2 minutes, rinsed with deionized water and dried for 20 minutes in an oven set at 105° C. The dried screen was cooled in a desiccator and re-weighed. Two tests were run for each sample and the results were averaged and expressed in mg lost per 100,000 revolutions. The result for a 10% silica slurry, measured in units of mg lost per 100,000 revolutions, can be characterized as the 10% brass Einlehner (BE) abrasion value.

Silica structure as used herein is described in the article "Cosmetic Properties and Structure of Fine-particle Synthetic Precipitated Silicas", S. K. Wason, in the *Journal of Soc. Cosmet. Chem.*, Vol. 29, (1978), pp. 497–521, which is incorporated herein by reference. Such inventive compositions include silica particles that exhibit a linseed oil absorption value of from about 50 ml/100 g to about 90 ml/100 g.

EXAMPLE 1

A batch of amorphous precipitated silica was prepared in a reactor as follows, which thereafter was subjected to certain dewatering, wet milling and particle classification described below, without any drying or dry milling occurring, to observe the effects of the post-processing procedures that were applied.

The batch was prepared by adding 502 gallons (1900 L) of sodium silicate (13.0%, 2.50 mole ratio of $SiO_2:Na_2O$,) to a reactor and heated it to 85° C. Then sodium silicate (13.0%, 2.50 mole ratio of $SiO_2:Na_2O$, preheated to 85° C.) and sulfuric acid (11.4%) were simultaneously added to the reactor at a rate of 102.4 gpm (387.6 L/min) and 45.0 gpm (170.3 L/min). The simultaneous addition of sodium silicate and sulfuric acid continues for 48 minutes, after which time the sodium silicate addition is discontinued. The acid flow was continued until the batch pH dropped to 5.2, at which time the acid flow was stopped. The batch was then digested at 93° C. for 10 minutes, with the pH adjusted back towards 5.2 as needed throughout digestion. After digestion, the pH was manually adjusted to 5.1±0.1, and the batch was discharged from the reactor into a filter feed tank.

The batch was filtered on a pressure filter press (model JVAP 470/100 available from US Filter Corporation, Holland, Mich.) to 33–34% solids and then the press cake was fed into a Premier bead mill (model HML-1.5 available from Lightnin, Inc., Reading, Pa.) at a rate of 0.43 liters per minute (LPM). The Premier mill is a horizontal style media mill, having a 1.5 liter grinding chamber which was loaded with 1.06 liters of 0.8–1.0 mm sized zirconia media beads having a specific gravity of 3.7. The silica was passed through the mill three times with an aliquot collected after each pass to measure particle size characteristics. The particle size properties of the starting feed and bead milled materials measured according to the methods described above are summarized below in Table 1.

TABLE 1

| Pass No. | MPS, μm | Span |
| --- | --- | --- |
| Starting Feed | 15.34 | 3.10 |
| 1 | 0.87 | 5.77 |
| 2 | 0.47 | 3.61 |
| 3 | 0.46 | 2.87 |

It is seen in Table 1 that bead milling was effective to reduce the particle size of Example 1 silica from about 15 μm to about 0.5 μm.

Next, the milled press cake from the third pass was split into 2 portions which were separately fed into a Sharples BM-PF743/54893C3 decanter/centrifuge under the conditions summarized in Table 2 below.

In the first trial, five gallons of the bead milled silica prepared above was diluted with 15 liters of water in the feed tank (20% solids) and mixed. Four separate trials (Trial 1A–1D) were conducted under the centrifuge/decanter conditions given in Table 2. The centrifuge/decanter was configured to recirculate both the overflow and underflow streams. Recirculation continued for the duration of the Trials 1A through 1D.

In the second trial, five gallons of the bead milled silica prepared above was diluted with 50 liters of water to 9.8% solids and mixed. The centrifuge/decanter was configured to recirculate both the overflow and underflow streams for the duration of separate Trials 2A through 2D. At the end of the Trial 2D, recirculation was turned off so that the overflow stream could be collected for Trial 3.

In Trial 3, ten gallons of the overflow material from Trial 2D (9.8% solids) was fed into the centrifuge/decanter configured so that the overflow was recirculated and the underflow was discarded. The centrifuge was run at 60 Hz with samples collected for particle size analysis every 0.5 hour from 2 to 4 hours.

TABLE 2

| Trial No. | Centrifuge Time, Hr | % Solids | Hz | Feed Rate LPM |
|---|---|---|---|---|
| 1A | 0.5 | 20 | 60 | 0.5 |
| 1B | 0.5 | 20 | 30 | 1 |
| 1C | 0.5 | 20 | 60 | 1 |
| 1D | 0.5 | 20 | 30 | 0.5 |
| 2A | 0.5 | 9.8 | 60 | 0.5 |
| 2B | 0.5 | 9.8 | 30 | 1 |
| 2C | 0.5 | 9.8 | 60 | 1 |
| 2D | 0.5 | 9.8 | 30 | 0.5 |
| 3A | 0 | 9.8 | 60 | 0.5 |
| 3B | 2 | 9.8 | 60 | 0.5 |
| 3C | 2.5 | 9.8 | 60 | 0.5 |
| 3D | 3.0 | 9.8 | 60 | 0.5 |
| 3E | 3.5 | 9.8 | 60 | 0.5 |
| 3F | 4 | 9.8 | 60 | 0.5 |

Particle size characteristics of materials from Trials 1, 2 and 3 measured according to the methods described above are summarized in Table 3.

TABLE 3

| Trial No. | MPS, μm | Span |
|---|---|---|
| 1A | 0.28 | 0.72 |
| 1B | 0.41 | 2.33 |
| 1C | 0.28 | 0.75 |
| 1D | 0.32 | 0.90 |
| 2A | 0.28 | 0.83 |
| 2B | 0.40 | 1.90 |
| 2C | 0.33 | 0.96 |
| 2D | 0.37 | 1.40 |
| 3A | 0.36 | 1.45 |
| 3B | 0.19 | 0.58 |
| 3C | 0.17 | 0.59 |
| 3D | 0.17 | 0.58 |
| 3E | 0.16 | 0.59 |
| 3F | 0.15 | 0.59 |

It is seen that centrifuging this bead milled silica was effective to isolate fractions of smaller particle size materials, even as small as 0.15 μm with a very narrow particle size distribution as indicated by a small span value.

EXAMPLE 2

A portion of the silica prepared in Example 1 was collected after the reactor, filtered and washed to remove sulfate, then the filter cake was fed at a rate of 0.8 LPM into a 1.5 liter horizontal style media mill (model HML 1.5 Premiere Mill manufactured by Lightnin, Inc., Reading, Pa.) loaded with 1080 ml of 1.6 mm zirconia beads having a specific gravity of 3.7 and set to a speed of 2500 FPM (feet per minute) to reduce the particle size. The silica feed (Example 2A) to the mill had a MPS of 10.8 μm and a distribution span of 4.8. After milling the silica denoted as Example 2B had a MPS of 5.79 μm, a span of 2.31 and was at 34.9% solids. Next, the milled slurry was fed into a 6" solid bowl continuous flow 6,000 rpm Bird centrifuge (BIRD Machine Company Inc., South Walpole, Mass.) in order to collect a fraction of particles with a MPS of about 6 μm. The silica slurry was fed into the centrifuge at a rate of 8.9 LPM with the centrifuge set to 40 HZ. The overflow was collected and fed beck into the centrifuge (60 HZ) at a rate of 3 LPM. From this classification, the underflow was collected as Example 2C and fed to a J-Vap dewatering system (model JVAP 470/100 available from US Filter Corporation, Holland, Mich.) for dewatering the silica slurry. The slurry feed was at 45% solids before dewatering and at 90% solids afterwards. The dewatered silica from the J-Vap dewatering system is denoted as Example 2D. The J-Vap dewatering conditions are summarized in Table 4.

TABLE 4

| J-Vap Dewatering Conditions | |
|---|---|
| Fill | |
| Pressure, psig | 80 |
| Slurry Temp., ° C. | 67 |
| Volume, L | 7.5 |
| Time, min | 2 |
| 1rst Blow Down (BD) | |
| BD P, psig | 20 |
| BD Time, min | 2 |
| Core Blow Down (BD) | |
| P, psig | 80 |
| Volume, L | 1 |
| BD Time, sec | 15 |
| Number BD | 3 |
| 2nd Blow Down (BD) | |
| P, psig | 60 |
| Volume, L | 1 |
| Time, min | 10 |
| Squeeze | |
| P, psig | 95 |
| Water Temp., ° C. | 85 |
| Vacuum, inch Hg | 28 |
| Dry Time, hr | 5 |
| Cake Solids, % | 90.03 |
| Cake Weight, kg | 7.5 |

Finally, the material was discharged from the J-Vap dewatering system and then fed into a Raymond mill configured with no hammers or whizzards to gently de-agglomerate the particles. The de-agglomerated particles are designated as Example 2E.

Another portion of the silica of Example 1 was collected after the reactor then filtered, washed, spray dried and milled (2 Control) to be used as a dry silica control representing conventionally prepared precipitated silica.

Properties of the silicas from all stages of Example 2 and the conventionally prepared silica "Control 2" were measured according to the procedures described above and are summarized below in Table 5.

TABLE 5

| Example | 2A | 2B | 2C | 2D | 2E | 2 Control |
|---|---|---|---|---|---|---|
| % Solids | 34.9 | 34.9 | 45.0 | 91.5 | 95.1 | 95.8 |
| MPS, μm | 10.8 | 5.8 | 6.0 | 7.2 | 6.3 | 8.3 |
| Span | 3.69 | 2.31 | 1.94 | 2.07 | 1.69 | 1.95 |
| % 325 Mesh Residue | — | — | 0.04 | 2.37 | 0.02 | 0.00 |
| 5% pH | — | — | 7.3 | 7.9 | 7.8 | 7.1 |
| Pore Volume, ml/g | — | — | 1.14 | 1.25 | 1.57 | 1.76 |
| Oil Absorption, ml/100 g | — | — | — | 75 | 78 | 91 |
| Pack Density, g/ml | — | — | — | 0.64 | 0.50 | 0.42 |
| Pour Density, g/ml | — | — | — | 0.45 | 0.24 | 0.21 |
| BE, mg loss/100,000 rev | — | — | 3.0705 | — | 6.9345 | 5.0485 |
| Brightness | — | — | 99.6 | 99.5 | 97.8 | 96.0 |

The data summarized in Table 5 above shows that the inventive process was effective to provide a silica product with sequentially reduced silica median particle size and a narrow particle size distribution (span) by bead milling the silica slurry, classifying the resulting slurry and then dewatering and gently de-agglomerating the resulting silica product without any intervening expensive drying (spray or nozzle drying) step. It is surprising to note that Example 2E produced by the inventive process has a lower oil absorption value, higher Brass Einlehner value and is more dense than conventionally produced silica (Control 2) indicating the inventive process produces a lower structure, more abrasive silica. Also surprisingly, the inventive silica Examples 2C–2E have a higher brightness value than the conventionally produced Control 2 silica showing that the inventive silicas, while even lower structure (harder) than Control 2 silica, can be wet bead milled, classified, dewatered and de-agglomerated to essentially the same size as the conventional silica without intensive dry milling, resulting in a loss in brightness. The silica product can be used in the slurry form from step 2C or used as a dewatered and de-agglomerated silica containing as little as about 5% moisture from step 2E.

EXAMPLE 3

This batch of amorphous precipitated silica was prepared by adding 474 gallons (1794 L) of sodium silicate (13.30%, 2.65 mole ratio of $SiO_2:Na_2O$) to a reactor and heating it to 85° C. Then, simultaneous addition of sodium silicate (13.3%, 2.65 mole ratio of $SiO_2:Na_2O$, preheated to 85° C.) at a rate of 92.7 gpm (351 L/min) and sulfuric acid (11.4%) at a rate of 41.5 gpm (157 L/min) was continued for 47 minutes, after which time the sodium silicate addition was discontinued. The acid flow was continued until the batch pH dropped to 5.9±0.1, at which time the acid flow was discontinued. The batch was then digested at 93° C. for 10 minutes, with the pH adjusted back towards 5.9 as needed throughout digestion. After digestion, the pH was manually adjusted to 5.9±0.1, and the batch was discharged from the reactor.

Example 3 silica had a 5% pH of 7.75, a sodium sulfate content of 0.9%, an oil absorption of 73 ml/100 g and a median particle size of 27 μm.

Example 3 silica prepared as described above was diluted to 40% solids with water and split into several portions for post reaction particle size reduction in a Denver mill (Denver Equipment, Colorado Springs, Colo.) and particle classification in a Bird solid bowl centrifuge available from Bird Machine Company, South Walpole, Mass.

Example 3 silica, having a median particle size of 27 μm before any milling commenced, was the starting silica fed to the mill for Examples 3A–3F. Example 3A, having a median particle size of 10.9 μm after milling and before any classification took place, was milled under the conditions given in the Table 6 and then was fed to the centrifuge under the conditions given for Examples 3B and 3C. Examples 3D–3F were milled and classified under the conditions shown in Table 6. The Denver mill and Bird centrifuge classification conditions used for each trial are summarized in Table 6.

TABLE 6

| | Mill Conditions | | | Centrifuge Conditions | |
|---|---|---|---|---|---|
| | Feed | | | | |
| Ex. No. | Rate LPM | % bead loading | Speed. HZ | Feed Rate LPM | RPM |
| 3A | 3.78 | 20 | 50 | NA | NA |
| 3B | 3.78 | 20 | 50 | 3.78 | 1440 |
| 3C | 3.78 | 20 | 50 | 2.84 | 1500 |
| 3D | 1.89 | 20 | 67.5 | 1.89 | 1440 |
| 3E | 1.89 | 20 | 70 | 1.89 | 1380 |
| 3F | 1.89 | 40 | 70 | 1.89 | 2240 |

Several properties of the silicas from each mill and classification trial were determined according to the methods described above and are summarized below in Table 7.

TABLE 7

| Example No. | Oil absorption ml/100 g | Mill MPS, μm | Centrifuge MPS, μm | Span | Centrifuge top size, μm |
|---|---|---|---|---|---|
| 3A | 76 | 10.9 | NA | NA | NA |
| 3B | 78 | 10.9 | 9.0 | 4.10 | — |
| 3C | 84 | 10.9 | 4.8 | 3.30 | — |
| 3D | 77 | 5.6 | 2.6 | 4.13 | 17.4 |
| 3E | 71 | 5.0 | 3.8 | 2.62 | 26.1 |
| 3F | 65 | 5.9 | 0.54 | 2.50 | 10.1 |

The milling was effective in reducing the median particle size from 27 μm to about 5 μm. Classification was effective to isolate a fraction of the particles having a narrow particle size distribution by removing large particles. The feed to the centrifuge had a top size of about 450 μm.

Dentifrice Formulations

Toothpaste formulations were prepared to demonstrate the ready-to-use on demand capabilities of the inventive abrasive particulate compositions. Dentifrices were formulated with the silica made by the inventive process, as described above, and other ingredients, in amounts indicated in grams, as described in TABLE 8 below. For comparison, the Control 2 dry silica prepared in Example 2 and Example 2B silica were separately incorporated in toothpaste formulations. Properties of these dentifrice formulations are given in TABLE 9 below.

To prepare the dentifrices, the following procedure was followed. The glycerin, sodium carboxymethyl cellulose (Cekol 2000 from the Noviant B.V., Nijmegen, The Netherlands) and sorbitol were mixed together and stirred until the ingredients were dissolved to form a first admixture. The deionized water, sodium fluoride, tetrasodium pyrophosphate and sodium saccharin were also mixed together and stirred until these ingredients are dissolved to form a second admixture. These two admixtures were then combined with stirring to obtain a "pre-mix".

The pre-mix was placed in a Ross mixer (Model 130 LDM) and abrasive silica and titanium dioxide were mixed in without vacuum. A 30-inch vacuum was drawn and the resultant admixture was stirred for approximately 15 minutes. Lastly, sodium lauryl sulfate and flavor were added and the admixture was stirred for approximately 5 minutes at a reduced mixing speed. The resulting dentifrice composition is sealed in toothpaste tubes and held under appropriate conditions for later testing.

TABLE 8

| Toothpaste No. | 1 | 2 | 3 | 4 |
|---|---|---|---|---|
| Glycerin, 99.5%, g | 11.600 | 11.600 | 11.600 | 11.600 |
| Sorbitol, 70.0%, g | 38.457 | 38.457 | 38.457 | 38.457 |
| Deionized Water, g | 25.000 | 0.600 | 25.000 | 0.000 |
| Cekol 2000 CMC, g | 1.200 | 1.200 | 1.200 | 1.200 |
| Tetrasodium pyrophosphate, g | 0.500 | 0.500 | 0.500 | 0.500 |
| Sodium Saccharin | 0.300 | 0.300 | 0.300 | 0.300 |
| Sodium Fluoride | 0.243 | 0.243 | 0.243 | 0.243 |
| Abrasive | | | | |
| Example 2E | 20.0 | — | — | — |
| Example 2C | — | 44.4 | — | — |
| Example 2 control | — | — | 20.0 | — |
| Example 2B | — | — | — | 45.0 |
| TiO$_2$, g | 0.500 | 0.500 | 0.500 | 0.500 |
| Sodium Lauryl Sulfate | 1.200 | 1.200 | 1.200 | 1.200 |
| Flavor | 1.000 | 1.000 | 1.000 | 1.000 |

The toothpaste properties described herein were measured as follows, unless indicated otherwise.

The toothpaste viscosity is measured utilizing a Brookfield Viscometer Model RVT equipped with a Helipath T-F spindle and set to 5 rpm by measuring the viscosity of the toothpaste at 25° C. at three different levels as the spindle descends through the toothpaste test sample and averaging the results. Brookfield viscosity is expressed in centipoise (cP).

The pH values of the toothpaste mixtures (25 weight %) encountered in the present invention can be monitored by any conventional pH sensitive electrode.

Aesthetic properties of toothpaste (stand-up, separation) were measured visually. About a one inch ribbon of toothpaste was squeezed from a tube onto a piece of ordinary white notebook paper. After waiting 3–5 minutes, aesthetic property observations were recorded.

Stand-up refers to the shape of the toothpaste ribbon and relates to the paste's ability to stay on top of a toothbrush without sinking in-between the bristles. A scale of 1–10 is used, with a 10 stand-up rating being good and meaning the ribbon retained its shape; a rating of 1 for stand-up is poor meaning the ribbons flattens out, losing its shape.

Separation refers to the toothpaste formulation's integrity. Solid and liquid phases of the toothpaste may separate, usually due to too little binder or thickener. Liquid will be visible around the squeezed ribbon of paste if there is separation. Separation ratings are on a scale of 1–10 with a rating of 10 meaning no separation; a rating of 1 meaning major phase separation; and intermediate ratings meaning that there an amount of liquid appears around ribbon.

The Radioactive Dentin Abrasion (RDA) values of the precipitated silica compositions used in this invention are determined according to the method set forth by Hefferen, Journal of Dental Res., July–August 1976, 55 (4), pp. 563–573, and described in Wason U.S. Pat Nos. 4,340,583, 4,420,312 and 4,421,527, which publications and patents are incorporated herein by reference.

The PCR test is described in "In Vitro Removal of Stain With Dentifrice" G. K. Stookey, et al., J. Dental Res., 61, 1236–9, 1982.

TABLE 9

| Toothpaste No. | 1 | 2 | 3 | 4 |
|---|---|---|---|---|
| 24 hr. Viscosity, cP | 190,000 | 210,000 | 190,000 | 220,000 |
| 1 Wk Viscosity, cP | 220,000 | 240,000 | 240,000 | 280,000 |
| 3 Wk Viscosity, cP | 260,000 | 280,000 | 250,000 | 300,000 |
| 6 Wk Viscosity, cP | 290,000 | 300,000 | 280,000 | 310,000 |
| 25% pH | 7.26 | 7.15 | 7.11 | 7.13 |
| RDA | 146 | 140 | 135 | 130 |
| PCR | 83 | 85 | 79 | 81 |

Toothpaste formulated with the inventive silica slurry compositions had good viscosity and aesthetic properties. The ability to provide moderate RDA levels with simultaneously high PCR measurements thus shows the benefits of such abrasive particle compositions in dentifrice formulations as well. Thus, the wet comminution with subsequent classification of resultant particles provides heretofore unmet benefits at least in terms of production complexity and lower overall production costs to provide a substantially similar product to those currently utilized within the dentifrice industry.

It will be understood that various changes in the details, materials, and arrangements of the parts which have been described and illustrated herein in order to explain the nature of this invention may be made by those skilled in the art without departing from the principles and scope of the invention as expressed in the following claims.

What is claimed is:

1. A method of providing a particulate composition, said method comprising the sequential steps of:
   a) providing a plurality of particles selected from the group consisting of precipitated silica particles, silica gel particles, precipitated calcium carbonate particles, calcium pyrophosphate particles, dicalcium phosphate, and any mixtures thereof;
   b) subjecting said plurality of particles to a comminuting step in a wet environment;
   c) subjecting said wet-comminuted particles of step "b" to a particle size classification step wherein particles exhibiting a median particle size range of from about 5 to about 30 microns are collected;
   d) subjecting said collected particles from step "c" to a subsequent particle size classification step wherein particles exhibiting a median particle size range of from about 5 to about 15 microns are collected; optionally
   e) subjecting said collected classified particles from step "d" to a dewatering step wherein said dewatered particles exhibit a moisture content of at most 60 wt %; and, optionally
   f) subjecting said dewatered abrasive particles to a deagglomeration step.

2. The method of claim 1 wherein said collected classified particles of step "d" exhibit a particle size span of less than or equal to 2.

3. The method of claim 2 wherein step "e" is present.

4. The method of claim 3 wherein step "f" is present.

5. The method of claim 2 wherein said particles are amorphous precipitated silica particles and step "a" comprises the admixing of a sufficient amount of an alkali silicate and an acidulating agent to form precipitated silica particles.

6. The method of claim 2 wherein said collected classified particles from step "d" exhibit a median particle size of about 6 to about 10 microns and a particle size span of from about 1.25 to about 2.0.

7. The method of claim 6 wherein step "e" is present.

8. The method of claim 7 wherein step "f" is present.

9. The method of claim 6 wherein said particles are amorphous precipitated silica particles and step "a" comprises the admixing of a sufficient amount of an alkali silicate and an acidulating agent to form precipitated silica particles.

10. The method of claim 6 wherein said collected classified particles from step "d" exhibit a median particle size of about 7 to about 9 microns, a particle size span of from about 1.25 to about 1.95.

11. The method of claim 10 wherein step "e" is present.

12. The method of claim 11 wherein step "f" is present.

13. The method of claim 10 wherein said particles are amorphous precipitated silica particles and step "a" comprises the admixing of a sufficient amount of an alkali silicate and an acidulating agent to form precipitated silica particles.

14. The method of claim 1 wherein step "e" is present.

15. The method of claim 14 wherein step "f" is present.

16. The method of claim 15 wherein said particles are amorphous precipitated silica particles and step "a" comprises the admixing of a sufficient amount of an alkali silicate and an acidulating agent to form precipitated silica particles.

17. The method of claim 14 wherein said particles are amorphous precipitated silica particles and step "a" comprises the admixing of a sufficient amount of an alkali silicate and an acidulating agent to form precipitated silica particles.

18. The method of claim 1 wherein said particles are amorphous precipitated silica particles and step "a" comprises the admixing of a sufficient amount of an alkali silicate and an acidulating agent to form precipitated silica particles.

* * * * *